United States Patent [19]

Jewell

[11] 4,284,508

[45] Aug. 18, 1981

[54] METHANE PRODUCTION BY ATTACHED FILM

[76] Inventor: William J. Jewell, 202 Eastwood Ave., Ithaca, N.Y. 14850

[21] Appl. No.: 80,559

[22] Filed: Oct. 1, 1979

[51] Int. Cl.³ ............................................. C02F 3/28
[52] U.S. Cl. .................................. 210/603; 210/612; 210/617
[58] Field of Search ..................... 210/2, 8, 16, 17, 20, 210/150, 603, 605, 612, 613, 615–618, 630, 661, 795; 435/801

[56] References Cited

U.S. PATENT DOCUMENTS

| | | | |
|---|---|---|---|
| 4,032,407 | 6/1977 | Scott et al. | 195/127 |
| 4,127,447 | 11/1978 | Griffith et al. | 435/801 X |
| 4,182,675 | 1/1980 | Teris | 210/8 |

FOREIGN PATENT DOCUMENTS 2013170 8/1979 United Kingdom ..................... 210/2

OTHER PUBLICATIONS

Pitt et al., "The Tapered Fluidized Bioreactor, etc.", AICHE Symposium Series No. 181, vol. 74 (1978).
Holladay et al., "Biodegradation of Phenolic Waste Liquors, etc.", AICHE Symposium Series, vol. 74, No. 172, pp. 241–252 (1978).
Scott et al., "Use of a Tapered Fluidized Bed as a Continuous Bioreactor", Biotechnology & Bioengineering, vol. 18, pp. 1393–1403 (1976).
Hsu, "Characteristics of Tapered Fluidized Reactors, etc.", paper presented at symposium on Biotechnology, etc., Gatlinburg, Tenn., May 10–12, 1978.

Primary Examiner—Thomas G. Wyse
Attorney, Agent, or Firm—Laubscher & Laubscher

[57] ABSTRACT

A method for purifying wastewater of biodegradable organics by converting the organics to methane and carbon dioxide gases is disclosed, characterized by the use of an anaerobic attached film expanded bed reactor for the reaction process. Dilute organic waste material is initially seeded with a heterogeneous anaerobic bacteria population including a methane-producing bacteria. The seeded organic waste material is introduced into the bottom of the expanded bed reactor which includes a particulate support media coated with a polysaccharide film. A low-velocity upward flow of the organic waste material is established through the bed during which the attached bacterial film reacts with the organic material to produce methane and carbon dioxide gases, purified water, and a small amount of residual effluent material. The residual effluent material is filtered by the film as it flows upwardly through the reactor bed. In a preferred embodiment, partially treated effluent material is recycled from the top of the bed to the bottom of the bed for further treatment. The methane and carbon dioxide gases are then separated from the residual effluent material and purified water.

12 Claims, 1 Drawing Figure

U.S. Patent  Aug. 18, 1981  4,284,508
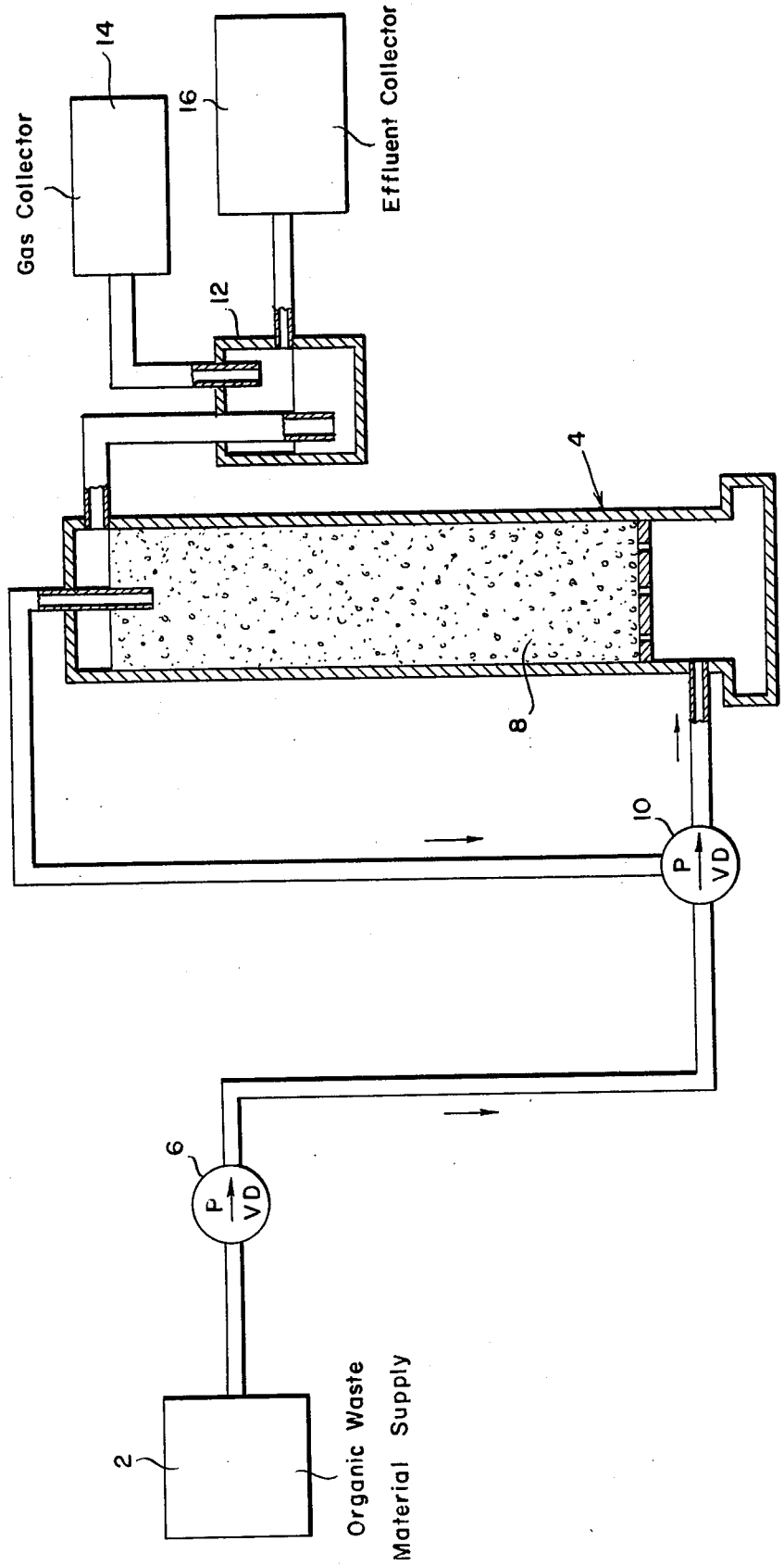

METHANE PRODUCTION BY ATTACHED FILM

BRIEF DESCRIPTION OF THE PRIOR ART

Soluble and particulate colloidal organics in domestic and industrial wastewater are normally converted to carbon dioxide and sludge using aerobic microbiological treatment processes. Aeration processes commonly used in the United States to provide the necessary oxygen for such alternatives as activated sludge treatment of domestic sewage consume an amount of energy exceeding $100.00 per million gallons of wastewater or about half a billion dollars per year. Furthermore, aerobic processes synthesize large amounts of sludge requiring further expensive treatment. In the activated sludge process, about half of the biochemical oxygen demand that is removed from the water is converted to new microbial biomass that becomes waste sludge which is difficult to handle, stabilize, and dispose. The energy content of the waste organics in sewage has an energy value of about $100.00 per million gallons. Although the conversion of these organics to substitute natural gas (a mixture of methane and carbon dioxide) is known to be possible with anaerobic fermentation using methane forming bacteria, together with other polymer destroying bacteria in a heterogeneous culture, the various processes previously developed are severely limited because of their low removal rates and low efficiencies of conversion. The present invention was developed to eliminate these restrictions that apply to previous anaerobic processes.

Numerous attempts have been made to improve the organic conversion process with the most recent improvements focusing on the attached film processes using air or pure oxygen. Waste treatment methods and apparatus using a fluidized bed are well-known in the patented prior art as evidenced by the patents to Jeris, U.S. Pat. Nos. 3,846,289, 3,956,129, 4,009,099 and 4,009,105. U.S. Pat. Nos. 3,846,289 and 3,956,129 disclose a method and apparatus, respectively, for denitrifying waste water using a fluidized bed including a solid particulate carrier having a particle size from about 0.2 to 3 millimeters. U.S. Pat. Nos. 4,009,098 and 4,009,105 disclose a method and apparatus, respectively, for removing organic carbon from waste water to reduce biochemical oxygen demand using a fluidized bed having the same sized particulate carrier as set forth in U.S. Pat. Nos. 3,846,289 and 3,956,129. U.S. Pat. No. 4,009,099 discloses a method and apparatus for removing ammonia nitrogen from waste water using a fluidized bed.

Although the aforementioned processes provide improvements in the technology, their oxygen requirements and high flow rates result in similar energy consumption as in conventional technology. The aerobic processes also result in similar large quantities of sludge generation, including those used with the fluidized bed.

While the methods and apparatus of the prior Jeris patents normally operate quite satisfactorily, they are not suitable for the treatment of organic waste material to produce methane gas. This is due to the fact that the Jeris processes require a supply of oxygen for the organic conversion reactions, and oxygen is toxic to the methane forming bacteria. Furthermore, the size and density of the particulate carrier material of the Jeris disclosures precludes a low velocity flow and is therefore not suitable for methane production and does not afford adequate control of bacterial growth within the expanded bed reactor to regulate the reaction process to maximize efficiency.

The present invention was developed to overcome the aforementioned difficulties by providing a method for the production of methane gas from dilute organic waste material using an anaerobic reaction process in an anaerobic attached film expanded bed reactor. The process permits the maintenance of high SRT (sludge retention time) values and low HRT (hydraulic retention time) values. The process is an energy producing wastewater purification system that minimizes excess sludge production and energy inputs.

SUMMARY OF THE INVENTION

Accordingly, it is a primary object of the present invention to provide a method for purifying waste water containing biodegradable organics which minimizes the waste sludge output and the energy input. Methane and carbon dioxide gases are produced from dilute organic waste material seeded with a heterogeneous anaerobic bacteria culture including a methane-producing bacteria when the waste material is introduced into the bottom of an anaerobic attached film expanded bed reactor including a particulate support media having a microbial film coated thereon. The organic waste material flows upwardly at a low velocity through the bed during which the attached bacteria multiply and convert the organic material into methane and carbon dioxide gases, and the film filters the remaining effluent material. The methane gas is then separated from the effluent material, whereby a continuous supply of methane gas is produced from a continuous supply of organic waste material.

According to a more specific object of the invention, partially treated effluent material at the top of the fluidized bed is recycled to the bottom of the bed for further treatment. The rate of recycling the partially treated effluent material may be used to control the upward flow of organic waste material through the expanded bed.

According to a further object of the invention, the upward flow rate of organic waste material through the expanded bed is from 0.1 to 8 gallons per minute per square foot [gal/min(ft$^2$)] and preferably from 2 to 4 gal/min(ft$^2$).

It is another object of the invention to provide a method for producing methane gas wherein the particulate support media within the reactor comprises a water-insoluble inorganic biomaterial having a diameter of from 5 to 200 microns and preferably about 20–30 microns.

According to a further object of the invention, a particulate support media is provided having a bulk density of generally 0.25–0.6 gm/cm$^3$ and a particulate density of generally 1.05–1.2 gm/cm$^3$.

A further object of the present invention is that the method may be used to treat organic slurries of sewage sludge, animal wastes, algae, and other finely ground biomass such as giant seaweed. The recycle flow rate and particulate size and density characteristics can be varied in order to allow the particulate organic solids to pass while maintaining the microbial coated particles within the reactor. In this case, heat may be added to the reactor to achieve a mesophilic (i.e., about 35° C.) or a thermophilic (i.e., about 43°–65° C.) methane production system. This would occur only with concentrated organic slurries that contain far more energy than necessary to heat the waste water. No heat requirement is necessary when treating dilute solutions of organics and wastewater such as domestic sewage.

BRIEF DESCRIPTION OF THE FIGURE

Other objects and advantages will become apparent from a study of the following specification when viewed in the light of the accompanying drawing which is a diagrammatic representation of the method for converting organics from waste water into methane and carbon dioxide gases.

DETAILED DESCRIPTION

The method for producing methane gas by the present invention is suitable for the treatment of any suitable dilute organic waste material such as domestic sewage, sludge, or human and animal wastes. These materials contain the biologically decomposable organics necessary for methane production such as cellulose, protein, or carbohydrates. The dilute organic waste materials have a concentration range of generally 20-60,000 mg/l BOC (biochemical oxygen demand) or 30-100,000 mg/l COD (chemical oxygen demand). Preferably, the waste materials contain about 50-600 mg/l BOD, as in the case with most domestic sewage and organic industrial wastes. Generally, anaerobic treatment has not been regarded as an effective process for treatment of low strength wastes. However, the use of an anaerobic attached film expanded bed reactor has provided an efficient process for treating dilute organic wastes by removing BOD and converting it to energy in the form of methane gas.

Referring now to the drawing, the general process for producing methane gas from dilute organic waste material will be described. A supply 2 of dilute organic waste material is delivered to the bottom of an anaerobic attached film expanded bed reactor 4 by a pump 6. The reactor includes a bed of particulate support media 8 through which the waste material flows. As will be developed in greater detail below, the organic waste material is converted within the expanded bed into methane gas and a residual effluent material. A portion of the partially treated effluent material may be recycled from the top of the bed to the bottom of the bed by the recycle pump 10 at a rate from a fraction of the inflow rate to ten times the inflow rate. The pumps 6 and 10 each have a variable delivery control to control the flow of waste material upward through the bed. If desired, the force of gravity may be used in place of the pump 6. The mixture of effluent material and methane gas is drawn off at the top of the reactor 4, where there is an interface of support media, effluent, and gas, into an inverted siphon 12 where the methane gas and effluent material are separated for delivery to a gas collector 14 and an effluent collector 16, respectively.

Although dilute organic waste material often contains a small amount of methane-producing bacteria, it is preferable to seed the reactor with a material contaning a heterogeneous bacteria culture including a methane-producing bacteria at the start-up of the reactor. One such material is anaerobically digested sludge and bovine rumen fluid. Gradually, after seeding the reactor, the methane-producing bacteria and other polymer destroying bacteria will form a uniform coating or film around each inert particle of the support material. The reactor is operated in a batch basis with the recycle effluent providing the expansion force for the bed. The start-up process normally takes several weeks, and after the reactor begins to produce gas with a methane content of greater than 50% by volume, continuous flow may be initiated.

The particulate support media 8 arranged in the anaerobic attached film expanded bed 4 is preferably a porous water-insoluble inorganic biomaterial such as aluminum oxide. Small glass beads may also be used for the support material. The particles are preferably of a uniform size and density for uniform flow of the waste material therethrough. The diameter of each particle is generally between 5 and 200 microns, but preferably 20-30 microns. The particle density of the support media is between 1.05 and 1.2 gm/cm$^3$ and the bulk density of the media is between 0.25 and 0.6 gm/cm$^3$. The support media particulates in the expanded bed are generally lighter and smaller than those used in prior waste treatment expanded bed devices. As shown in the drawing, organic waste material is pumped into the bottom of the anaerobic attached film expanded bed 4 and flows upwardly through the support media 8. The upward flow of the waste material expands the bed by approximately 20%. Because of the smaller, lighter particulate support media 8, the waste material flows upwardly at a relatively low velocity of from 0.1 to 8 gal/min/ft$^2$ and preferably between 2 and 4 gal/min/ft$^2$. Depending on the degree of completion of the conversion of organics to methane, and on the waste particle characteristics, the usual retention time within the reactor can be as low as ten minutes. In general, the reaction will largely be completed at retention times of thirty minutes for domestic sewage and six to nine hours for sludges and animal wastes. The rate of flow of material through the expanded bed may be controlled by the pumps 6 and 10 to account for varying biomass within the bed and to maintain a constant expanded level. Because of the low flow rate, the particulate support media forms a floating expanded bed through which the particles are evenly distributed. Furthermore, the low flow rate ensures that the bacteria are retained in the bed, as will be developed in more detail below.

To prepare the anaerobic attached film expanded bed for operation, small amounts of dilute organic waste material are gradually supplied to the bottom of the expanded bed after the bed has been innoculated as set forth above. As the waste material is passed upwardly through the bed, partial reaction of the waste material occurs at an operating temperature of between 4° and 30° C. and preferably between 18° and 30° C. The partial reaction initiates a growth of film on the surface of the particulate support material. The film is formed of polysaccharide or glycocalx material which has a web-like appearance when viewed through an electron microscope. Slow growth of the film continues until the desired amount of film is present within the expanded bed indicating that the anaerobic attached film expanded bed is ready for full operation.

During operation, as the dilute organic waste material flows upwardly through the bed, the heterogeneous bacteria attaches to the support media. Because of the smaller and lighter particles of support media and the low flow rate through the bed, the bacteria are less likely to be displaced from the film and removed from the system which greatly enhances the efficiency of the bed thereby maximizing methane production.

Within the bed, the heterogeneous bacteria culture converts the organic waste material to methane gas. Specifically, four groups of bacteria successively break down the organics as they flow upwardly through the system. The first group of bacteria breaks down the particulate organic material to soluble material. The second group of bacteria breaks down the soluble material into volatile acids, and the third group of bacteria breaks down the volatile acids into methane, hydrogen, and carbon dioxide. Finally, the fourth group of bacteria, which is the methane-producing bacteria, converts the hydrogen and carbon dioxide into methane gas as well as some of the volatile acids.

The expanded bed acts as a filter for the waste material and slows down the particulate support media. Partially treated effluent from the organic waste material collects at the top of the expanded bed. In a preferred embodiment, this material is recycled to the bottom of the bed for further treatment.

Upon completion of the treatment of the organic waste material, a mixture of gas and effluent material is delivered to an inverted siphon 12. There, methane gas and carbon dioxide are separated from the effluent material comprising stabilized sludge and purified water. New bacteria resulting from the treatment remain in the expanded bed attached to the film. Thus, as more waste material is treated, more anaerobic bacteria are accumulated in the expanded bed. The bacteria that grow in the expanded bed grow in relation to the type of organic product upon which they react. Thus, for example, if the organic waste material being treated has a high cellulose content, then more cellulose converting bacteria accumulate on the particles in the expanded bed. After prolonged use, the support media coated with the film of polysaccharide and bacteria may be removed from the reactor and used as a food source if desired.

Due to the low cell mass yield of anaerobic bacteria in the reactor, washing of newly synthesized sludge may not be necessary when treating domestic sewage in this process. Provided that a minimum of screening, and preferably primary sedimentation, precedes this process when applied to domestic sewage, it is anticipated that the effluent suspended solids will have a concentration less than 10 mg/l. This loss of solids will equal the bacterial yield, thus resulting in a system which has no sludge product. This compares to an oxygen system such as an activated sludge process or an oxygen fluidized bed which results in production of about 1200 pounds of waste bacteria per million gallons of waste water. For most sewage treatment facilities, this reduction in sludge production would lower processing costs by an additional $50–100.00 per million gallons treated.

While in accordance with the provisions of the Patent Statutes the preferred forms and embodiments of the invention have been illustrated and described, it will be apparent to those skilled in the art that various changes and modifications may be made without deviating from the inventive concepts set forth above.

What is claimed is:

1. A method for producing methane and carbon dioxide gases, comprising the steps of (a) seeding a dilute organic waste material with a heterogeneous bacterial culture including a methane-producing bacteria;
    (b) supplying said seeded waste material to an anaerobic attached film expanded bed reactor containing a particulate support media having a film coated thereon, said support media comprising porous water-insoluble inorganic biomaterial, each particle of which has a diameter of from about 5 to less than 200 microns;
    (c) establishing a low-velocity upward flow of said seeded waste material through said reactor to expand the bed of support media by about 20% through which the particulates of said support media are evenly distributed, said bacterial compound being attached to said film and reacting with said organic material to produce methane gas and residual, effluent material, said residual, effluent material being filtered by said film during upward flow therethrough; and
    (d) separating said methane gas from said effluent material, whereby methane gas is continuously produced from a supply of organic waste material.

2. A method as defined in claim 1, wherein partially filtered and treated waste material is recycled from the top to the bottom of said bed, said recycling of said material controlling said low-velocity upward flow.

3. A method as defined in claim 1, wherein said particulate support media comprises porous water-insoluble inorganic biomaterial.

4. A method as defined in claim 1, wherein the diameter of each particle of said support media is from about 20 to about 30 microns.

5. A method as defined in claim 4, wherein the particle density of said support media is generally from about 1.05 to about 1.20 gm/cm$^3$.

6. A method as defined in claim 5, wherein the bulk density of said support media is about 0.6 gm/cm$^3$.

7. A method as defined in claim 1, wherein said dilute organic waste material has a concentration of from about 30 to about 100,000 mg/l COD.

8. A method as defined in claim 7, wherein said dilute organic waste material has a concentration of from about 50 to about 600 mg/l COD.

9. A method as defined in claim 1, wherein said expanded bed reactor is operated at a temperature of from about 4° C. to about 30° C.

10. A method as defined in claim 9, wherein said expanded bed reactor is operated at a temperature of from about 18° C. to about 30° C.

11. A method as defined in claim 1, wherein said seeded waste material flows upwardly through said bed at a rate of from 0.1 to less than 6 gallons/minute/square foot.

12. A method as defined in claim 11, wherein said seeded waste material flows upwardly through said bed at a rate of from about 2 to about 4 gallons/minute/square foot.

* * * * *